United States Patent
Farrugia et al.

(10) Patent No.: US 7,128,069 B2
(45) Date of Patent: Oct. 31, 2006

(54) METHOD AND APPARATUS FOR IMPROVING THE COMFORT OF CPAP

(75) Inventors: Steven Paul Farrugia, Lugarno (AU); Matthew Alder, Lemongrove (AU); Andrew Martin Price, Greystanes (AU); Ron Richard, Temecula, CA (US)

(73) Assignee: Resmed Limited, New South Wales (AU)

( * ) Notice: Subject to any disclaimer, the term of this patent is extended or adjusted under 35 U.S.C. 154(b) by 90 days.

(21) Appl. No.: 10/871,970

(22) Filed: Jun. 18, 2004

(65) Prior Publication Data
US 2005/0005937 A1   Jan. 13, 2005

(30) Foreign Application Priority Data
Jun. 20, 2003   (AU)   ............................... 2003903138

(51) Int. Cl.
*A61M 16/00*   (2006.01)

(52) U.S. Cl. ........................... 128/204.18; 128/204.21; 128/204.23

(58) Field of Classification Search ........... 128/204.18, 128/204.21, 204.23
See application file for complete search history.

(56) References Cited

U.S. PATENT DOCUMENTS

| | | | |
|---|---|---|---|
| 3,362,404 A | 1/1968 | Beasley | |
| 4,957,107 A * | 9/1990 | Sipin | 128/204.21 |
| 5,044,362 A | 9/1991 | Younes | |
| 5,107,830 A | 4/1992 | Younes | |
| 5,117,819 A * | 6/1992 | Servidio et al. | 128/204.18 |
| 5,134,995 A | 8/1992 | Gruenke | |
| 5,199,424 A * | 4/1993 | Sullivan et al. | 128/204.18 |
| 5,239,995 A | 8/1993 | Estes | |
| 5,259,373 A * | 11/1993 | Gruenke et al. | 128/204.23 |
| 5,368,019 A * | 11/1994 | Latorraca | 128/204.18 |
| 5,433,193 A | 7/1995 | Sanders | |
| 5,522,382 A | 6/1996 | Sullivan | |
| 5,535,738 A | 7/1996 | Estes | |
| 5,537,997 A * | 7/1996 | Mechlenburg et al. | 128/204.23 |
| 5,540,222 A | 7/1996 | Younes | |
| 5,551,419 A * | 9/1996 | Froehlich et al. | 128/204.23 |
| 5,598,838 A * | 2/1997 | Servidio et al. | 128/204.23 |
| 5,682,878 A * | 11/1997 | Ogden | 128/204.23 |
| 5,704,345 A | 1/1998 | Berthon-Jones | |
| 5,823,187 A | 10/1998 | Estes | |
| 5,845,636 A | 12/1998 | Gruenke | |
| 5,865,173 A | 2/1999 | Froehlich | |
| 5,868,133 A * | 2/1999 | DeVries et al. | 128/204.21 |
| 5,884,662 A | 3/1999 | Younes | |
| 5,927,274 A * | 7/1999 | Servidio et al. | 128/204.18 |
| 6,105,575 A | 8/2000 | Estes | |
| 6,305,372 B1 * | 10/2001 | Servidio | 128/204.21 |

(Continued)

FOREIGN PATENT DOCUMENTS

WO    WO 00/027021    5/2000

(Continued)

*Primary Examiner*—Aaron J. Lewis
(74) *Attorney, Agent, or Firm*—Gottlieb Rackman & Reisman

(57) ABSTRACT

A low-cost CPAP apparatus in which, upon detection of the transition from inhalation to exhalation, the blower motor is de-energized to allow it to freewheel. When the pressure in the patient mask (or whatever interface is utilized) reaches a minimum pressure level during exhalation, the motor is re-energized and its speed is controlled so to maintain the pressure at a level suitable for exhalation. Upon detection of the transition from exhalation to inhalation, the motor speed is increased to provide higher pressures in the patient mask suitable for inhalation.

1 Claim, 9 Drawing Sheets

U.S. PATENT DOCUMENTS

| | | |
|---|---|---|
| 6,345,619 B1 | 2/2002 | Finn |
| 6,484,719 B1 | 11/2002 | Berthon-Jones |
| 6,532,957 B1 | 3/2003 | Berthon-Jones |
| 6,532,960 B1 | 3/2003 | Yurko |
| 6,553,992 B1 | 4/2003 | Berthon-Jones |
| 6,705,315 B1 | 3/2004 | Sullivan |

2003/0121519 A1   7/2003   Estes

FOREIGN PATENT DOCUMENTS

| | | |
|---|---|---|
| WO | WO 02/026305 | 4/2002 |
| WO | WO 03/075989 | 9/2003 |

* cited by examiner

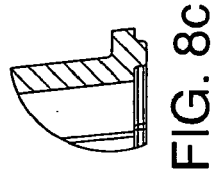
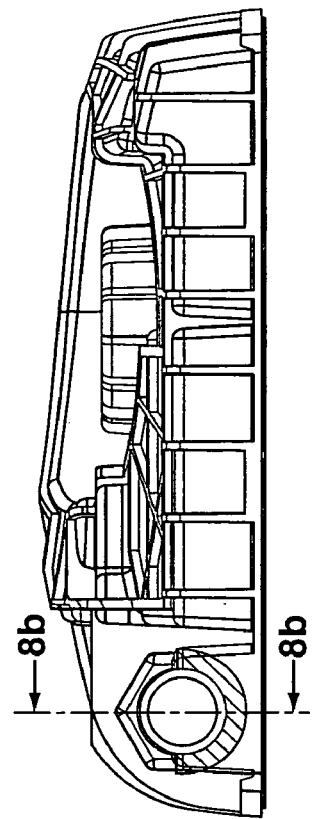
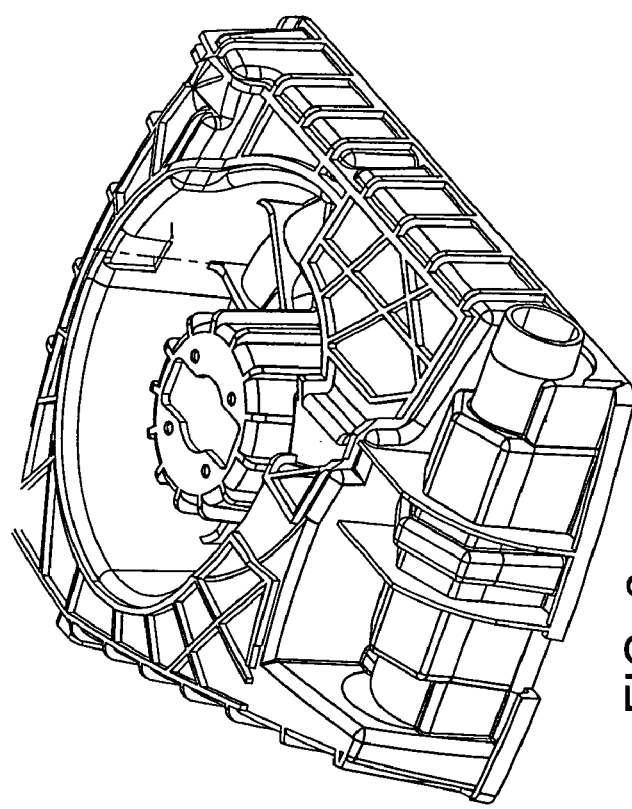
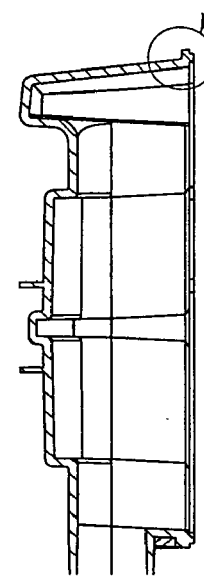

METHOD AND APPARATUS FOR IMPROVING THE COMFORT OF CPAP

This application claims the foreign priority of Australian provisional application No. AU 2003903138 filed on Jun. 20, 2003.

FIELD OF THE INVENTION

The invention relates to a method and apparatus for delivering a supply of air at positive pressure to a patient for treating sleep disordered breathing. In particular, the invention relates to a method and apparatus which provides a smooth, comfortable pressure versus time waveform.

BACKGROUND OF THE INVENTION

Since the invention of nasal Continuous Positive Airway Pressure (nasal CPAP) for treatment of Obstructive Sleep Apnea (OSA) and other forms of Sleep Disordered Breathing (SDB) by Sullivan, as taught in U.S. Pat. No. 4,944,310, much effort has been directed towards improving the comfort of the devices. One aspect of this is a more comfortable patient interface, such as provided by the MIRAGE® and ULTRA MIRAGE® masks manufactured by ResMed Limited. Another aspect of providing a more comfortable patient interface is the comfort of the waveform of air at positive pressure provided by the blower.

Some low cost CPAP blower devices, such as the S7™ device by ResMed Limited, provide a supply of air at a generally fixed positive pressure throughout the respiratory cycle of the patient, for example, 15 cmH2O. A blower comprising an electric motor and fan can be constructed to deliver air based on a rotational speed of the motor predetermined to deliver a particular pressure to a patient interface, such as a mask. When the patient breathes in with such a system, the pressure in the mask may reduce by a small amount. When the patient breathes out with such a system, the pressure in the mask may increase by a small amount. These fluctuations in mask pressure are referred to as "swing". Other blowers use feedback in a pressure controller which counterbalances the effect of patient effort on the mask pressure to reduces the swing. Such a device has a current retail price in Australia of approximately AU $1000.

Another group of CPAP devices, such as the ResMed AUTOSET® SPIRIT™ device can monitor the patient and determine an appropriate CPAP setting to deliver to the patient, which pressure may vary through the night, for example, delivering 15 cmH2O during an initial portion of the patient's sleep, but increasing to 20 cmH2O later in the night. Changes in pressure are made in response to a determination of the occurrence and severity of aspects of breathing such as flow limitation and snoring. Such a device has a current retail price in Australia of approximately AU $2000.

A bi-level CPAP device, such as the ResMed VPAP® product, provides a higher pressure to the patient's mask during the inspiratory portion of the respiratory cycle, for example, 10–20 cmH2O, and a lower pressure during the expiratory portion of the patient's breathing cycle, for example, 4–10 cmH2O. A mismatch between the device control cycle and the patient respiratory cycle can lead to patient discomfort. When the device makes a transition from the higher pressure to the lower pressure the motor is braked. When the device makes the transition from the lower pressure to the higher pressure, the motor is accelerated. Depending on device settings, the device may be required to make a change of 5–18 cmH2O pressure in 50–100 ms. To achieve this change, the peak power load may be in the order of 60–90 W. Because of the low inertia and peak load requirements of the VPAP® device, a large and expensive power supply is required. Such a device has a current retail price in Australia of approximately AU $3,500–7,500 depending on the device feature set.

U.S. Pat. No. 6,345,619 (Finn) describes a CPAP device that provides air at a pressure intermediate the IPAP (Inspiratory Positive Airway Pressure) and EPAP (Expiratory Positive airway Pressure) pressures during the transition between the inspiratory and expiratory portions of the device control cycle. U.S. Pat. Nos. 6,484,719 (Berthon-Jones) and 6,532,957 (Berthon-Jones) describe devices which provide pressure support in accordance with a waveform template. U.S. Pat. No. 6,553,992 (Berthon-Jones et al.) describes a ventilator whose servo-controller adjusts the degree of support by adjusting the profile of the pressure waveform as well as the pressure modulation amplitude. As the servo-controller increases the degree of support by increasing the pressure modulation amplitude, it also generates a progressively more square, and therefore efficient, pressure waveform; when the servo-controller decreases the degree of support by decreasing the pressure modulation amplitude, it also generates a progressively more smooth and therefore comfortable pressure waveform. The contents of all of these patents are hereby incorporated by reference.

CPAP and VPAP devices are mechanical ventilators. Ventilators have been classified (Chatburn, Principles and Practice of Mechanical Ventilation, Edited by M J Tobin, McGraw Hill, 1994, Ch. 2) as being either pressure, volume or flow controllers. In each case, the ventilator controls the pressure of air versus time, volume of air versus time, or flow of air versus time that is delivered to the patient. Many such devices can be programmed to deliver a variety of waveforms, such as pulse (rectangular), exponential, ramp and sinusoidal. The shape of the waveform actually delivered to the patient may be affected by the compliance and resistance of the patient's respiratory system and his breathing effort, as well as mechanical constraints such as blower momentum and propagation delays.

The Siemens Servo Ventilator 900B is a pneumatically powered ventilator which uses a scissor-like valve to control the inspiratory flow pattern (McPherson & Spearman, Respiratory Therapy Equipment, The C. V. Mosby Company, 1985, pp. 469–474).

Ventilators have been constructed to deliver an inspiratory waveform when one of pressure, volume, flow or time reaches a preset value. The variable of interest is considered an initiating or trigger variable. Time and pressure triggers are common. The Puritan Bennett 7200a ventilator is flow triggered. The Dräger Babylog ventilator is volume triggered. The Infrasonics Star Sync module allows triggering of the Infant Star ventilator by chest wall movement. The ventilator's inspiration cycle ends because some variable has reached a preset value. The variable that is measured and used to terminate inspiration is called the cycle variable. Time and volume cycled ventilators are known.

Many ventilators provide a Positive End-Expiratory Pressure (PEEP). Some of these ventilators use a valve (the PEEP valve) which allows the PEEP to be varied. Some devices, such as that taught by Ernst et al. in U.S. Pat. No. 3,961,627, provide a combination of pressure and flow control within one respiration cycle. A control cycle is divided into four phases I, II, III and IV. The respiration cycle and the control cycle do not necessarily have to fall together in time; mostly, however, phases I and II of the control cycle correspond to inspiration, and phases III and IV of the control cycle correspond to expiration. Phases I, III and IV are pressure-regulated, and phase II is flow-regulated. The doctor can choose the pressure course with the three control elements for the expiratory pressure decrease, the inflexion, and the final expiratory pressure. In phase III, the pressure proceeds from the pressure measured at the end of phase II according to a fixed pressure decrease dP/dt. When the pressure measured in phase III reaches the inflexion, the pressure proceeds linearly to the fixed final expiratory pressure. The part of the expiration from the inflexion to the end of the respiration cycle represents phase IV. The linear course of the pressure in the expiration represents a preferred embodiment, but could be replaced by another course of the pressure curve, for example, an exponential.

A spontaneously breathing patient exerts at least some effort to breath, however inadequate. A lack of synchrony between the respiratory cycle of the patient and that of the ventilator can lead to patient discomfort.

In Proportional Assist Ventilation (PAV), as described by Magdy Younes, the ventilator generates pressure in proportion to patient effort; the more the patient pulls, the higher the pressure generated by the machine. The ventilator simply amplifies patient effort without imposing any ventilatory or pressure targets. It is understood that the objective of PAV is to allow the patient to comfortably attain whatever ventilation and breathing pattern his or her control system sees fit. The PAV system is further discussed in U.S. Pat. Nos. 5,044,362, 5,107,830, 5,540,222 and 5,884,662.

In U.S. Pat. No. 5,044,362, Younes describes a system that operates as follows:

(a) Inspired flow: When the high frequency components of the output of a velocity transducer in a line are filtered out, the remaining signal agrees very well with flow measured independently at the airway. Accordingly, the velocity signal in the line is passed through a low pass filter and the resulting signal is used as a command signal for the ventilator unit to produce pressure in proportion to inspired flow, which is said to provide resistive assist. A gain control permits the selection of the magnitude of the assist. In practice, the flow signal is permanently connected to a summing amplifier and a minimum gain is set to offset the resistance of the tubing. When a greater assist is required to offset the patient's own resistance, the gain is increased.

(b) Inspired volume: The signal related to inspired flow may be integrated to provide a measure of inspired volume. A signal proportional to pressure is subtracted to allow for piston chamber compression. The magnitude of the pressure signal that is subtracted is a function of the gas volume of the system, according to Boyle's law. When the resulting signal is routed to the summing amplifier, the ventilator unit develops pressure in proportion to inspired volume. The magnitude of the assist obtained again may be controlled by a gain device.

(c) Ramp generator: This mode of operation permits the ventilator unit to function independent of patient effort and provides a controlled ventilation. This function can be activated by the operator throwing a switch to bring the function generator into the circuit. Alternatively, provision may be made for the ramp generator to be routed automatically to the summing amplifier in the event of the failure of the patient to breathe spontaneously for a specified period of time.

(d) D.C. output: An adjustable DC output provided by an offset amplifier also is routed to the summing amplifier, to result in the generation of continuous pressure.

U.S. Pat. No. 5,535,738 (Estes et al.) describes a further PAV apparatus.

Life support ventilators such as the Puritan-Bennett 7200a allow for a very precise control of the pressure, volume and flow rates of air delivered to patients. However such life support ventilators are too expensive for home use in treating sleep disordered breathing costing in the order of AU $50,000 to 100,000.

BRIEF SUMMARY OF THE INVENTION

In accordance with one aspect of the invention there is provided a low-cost CPAP apparatus that provides a more comfortable waveform of air for treatment of sleep disordered breathing.

In accordance with another aspect of the invention there is provided a low-cost CPAP apparatus for treatment of sleep disordered breathing that provides a reduced pressure of air during exhalation.

In accordance with another aspect of the invention there is provided a low-cost CPAP apparatus for treatment of sleep disordered breathing that reduces pressure during exhalation from a first level to a second level, the second level being no lower than a predetermined limit.

In accordance with another aspect of the invention there is provided a method of controlling the pressure developed by a blower by an electric motor comprising the step of freewheeling the motor when the pressure developed by the blower exceeds a threshold.

In accordance with another aspect of the invention, there is provided a CPAP apparatus which provides air at a first positive pressure during an inspiratory portion of a control cycle of the apparatus and air at a second positive pressure during an expiratory portion of a control cycle of the apparatus, and a smoothly varying pressure waveform between the inspiratory and expiratory portions of the control cycle.

In accordance with another aspect of the invention, there is provided a CPAP apparatus comprising an electric motor, a motor speed controller, an impeller (as used herein, an impeller is a rotating mechanism driven by a motor that blows air), a volute, a flow sensor, a controller, an air delivery conduit and a patient interface wherein:

(i) the CPAP apparatus is adapted to provide air at a first positive pressure in the patient interface during an inspiratory portion of a control cycle;

(ii) the flow sensor is adapted to measure the flow rate of air through the air delivery conduit;

(iii) the pressure sensor is adapted to measure the pressure of air in the patient interface;

(iv) the controller is adapted to detect a signal from the flow sensor indicative of the beginning of an expiratory portion of the respiratory cycle of the patient;

(v) upon detection of the beginning of the expiratory portion of the respiratory cycle, the controller is adapted to instruct the motor speed controller to freewheel the motor until the pressure in the patient interface falls to a predetermined level, and thereafter the controller instructs the motor controller to control the speed of the electric motor to deliver air at a second positive pressure; and (vi) upon detection of either an apnea or the beginning of the inspiratory portion of the patient's respiratory cycle, the controller is adapted to instruct the motor speed controller to accelerate the motor until the pressure in the patient interface reaches the first positive pressure in the patient interface.

Another aspect of the invention is to provide a CPAP apparatus with a low inertia motor. In accordance with this aspect, the motor inertia is sufficiently low so that the motor can freewheel from a first speed that delivered a first pressure level until a second predetermined pressure level is reached prior to the end of the expiratory cycle. In accordance with this aspect, the inertia of the motor is sufficiently low so that the rate of deceleration to the second predetermined pressure level is fast relative to the typical duration of exhalation. Preferably, the inertia of the motor and/or impeller is less than 13,600 g.mm$^2$. The net result is that a low-cost CPAP apparatus for treatment of sleep disordered breathing can be manufactured by having a blower driven by a motor provide air at a desired pressure at the airway of a patient in which the pressure during exhalation is reduced from a high level to a low level by allowing the motor to freewheel.

In another aspect of the invention, the first pressure level is determined in accordance with an automatic algorithm such as that described in U.S. No. Pat. 5,704,345.

Another aspect of the invention is to provide CPAP apparatus with a motor capable of delivering a more comfortable waveform of air.

Another aspect of the invention is to provide a CPAP comfort mode with a maximum pressure drop.

BRIEF DESCRIPTION OF FIGURES

FIGS. 8a–d shows further views of an upper volute suitable for use with an apparatus in accordance with an embodiment of the invention;

DETAILED DESCRIPTION OF THE INVENTION

Figure 1:
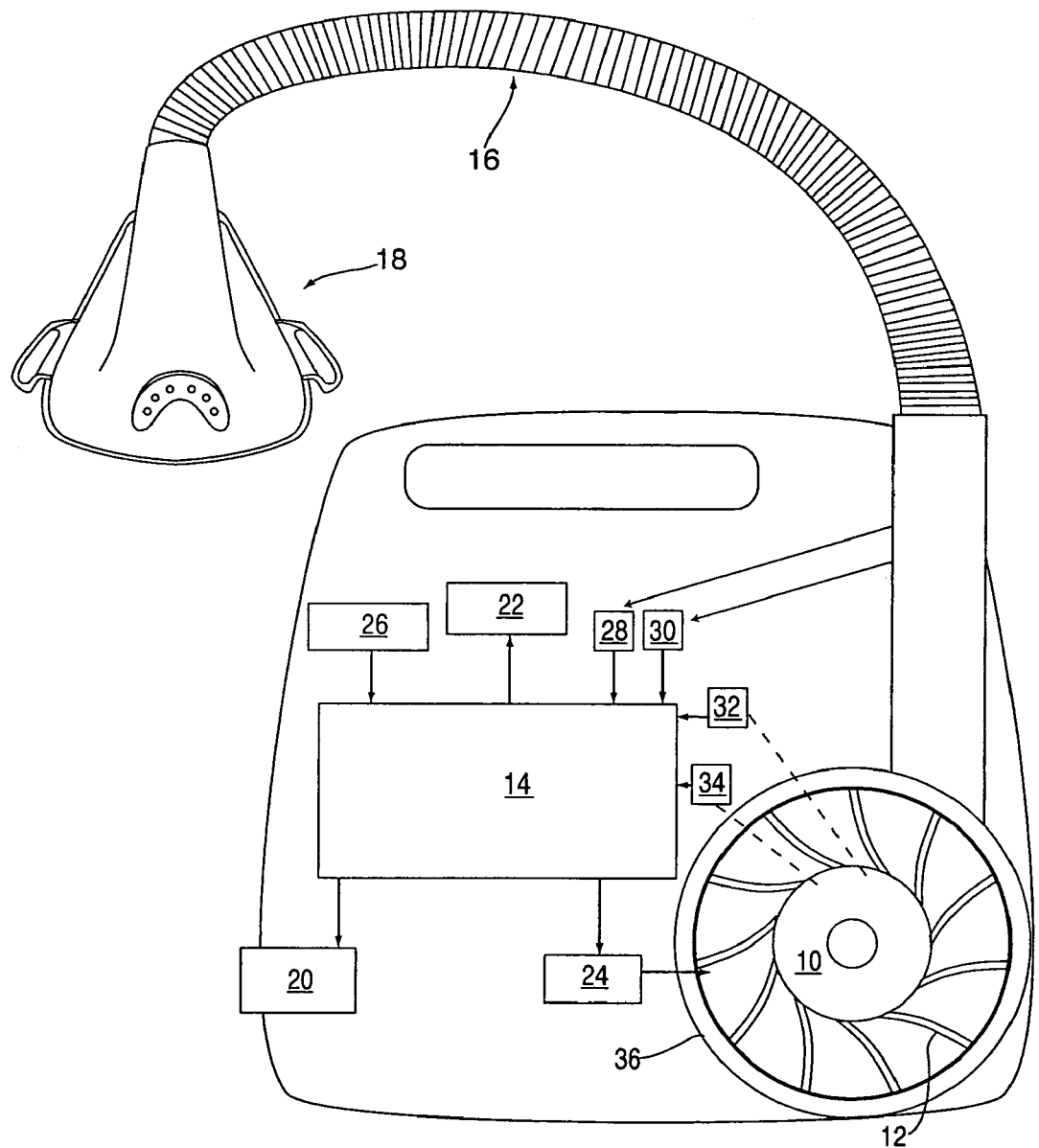
FIG. 1 shows CPAP apparatus in accordance with an embodiment of the invention.

FIG. 1 shows apparatus in accordance with an embodiment of our invention. A brushless electric motor 10 has an impeller 12 attached to it. The impeller 12 resides in a volute 36. The motor 10 is under the control of a motor controller 24 (suitable controllers include TMS320LC2402 or MC33035 IC). The motor includes sensors 32, 34 that provide signals indicative of motor rotational speed and current respectively. When the windings of the motor are energized, the impeller rotates. Air is drawn in through the inlet of the impeller and gains momentum. As the air passes out of the impeller and into the volute, it changes speed and develops pressure. Air passes out of the volute, past flow and pressure sensors 28, 30 (such as SM15652-003 flow sensor and SMI5652-008 or MPX2010 pressure sensors) respectively to an air delivery conduit 16 (for example, manufactured by Smooth-bor Plastics) that is in turn connected to a patient interface 18 which in the illustrated embodiment is a nasal mask, for example, a MIRAGE® or ULTRA MIRAGE® mask manufactured by ResMed Limited. Other forms of patient interface may be used, for example, a full-face mask, nasal prongs and nasal cushions.

The flow and pressure sensors 28, 30 provide data to a microcontroller 14. Suitable microcontrollers include the HITACHI SH 7032/34 which are 32-bit RISC devices, with a clock rate of 2–20MHz, 8 by 10 bit A-D converters and a variety of Input and Output features. The microcontroller 14 uses the Nucleus Plus Real-time Operating System (RTOS) by Accelerated Technologies Incorporated. In one form of the invention the apparatus delivers a predetermined CPAP pressure; such a device is the S7 ELITE by ResMed Limited. In another form of the invention the microcontroller 14 is programmed to deliver CPAP therapy in accordance with U.S. Pat. No. 5,704,345 (Berthon-Jones) which teaches a method and apparatus for detection of apnea and obstruction of the airway in the respiratory system. The contents of U.S. Pat. No. 5,704,345 are hereby incorporated by cross-reference.

The microcontroller 14 is programmed to detect the patient's transition between the inspiratory and expiratory portions of the patient's respiratory cycle. There are a number of ways of accomplishing this detection. One way is to monitor the flow of air to and from the patient. When the respiratory flow signal crosses zero (a "zero-crossing") there has been a transition between inspiration and expiration. Alternatively or additionally, the mask pressure may be monitored. When mask pressure falls below a first pressure threshold, inhalation is taken to have occurred. When mask pressure rises above a second threshold, exhalation is taken to have occurred. Alternatively or additionally, an effort sensor may be used on the patient, for example, to determine chest wall movements, movement of the supra-sternal notch or other patient movements (for example as described in U.S. Pat. No. 6,445,942). Measurement techniques may be combined with timed estimates of the period of a breath. For example, an average breath rate of the patient may be measured and when inhalation is detected by a flow, pressure or effort sensor, exhalation is assumed to occur after a period based on the measured average breath rate.

The apparatus includes a display 22, for example, a 2 line by 16 character LCD or similar display device. The apparatus includes a keypad 26, such as one using backlit silicone switches. The device also includes a power supply which provides 40 W at 24V with Class II isolation manufactured by SKYNET. The apparatus may include an interface 20 to enable communication with external devices. For example, a suitable interface chip is the MAX3130/MAX3131 from MAXIM. These chips provide both IrDA and RS-232 communication.

Figure 9C:
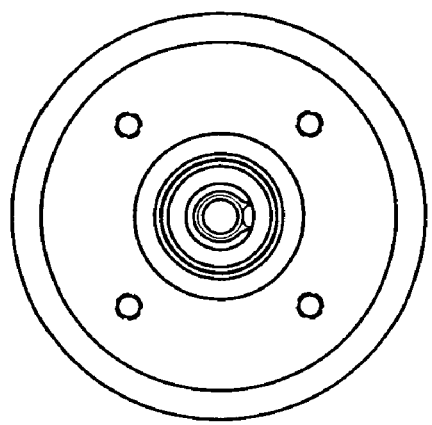
FIGS. 9a–c shows various views of a motor and impeller assembly suitable for use in apparatus in accordance with an embodiment of the invention.
Figure 9B:
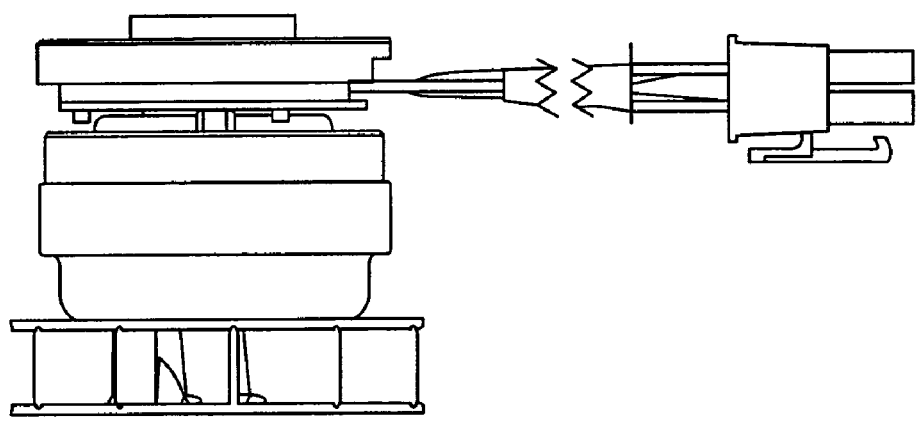
Figure 9A:
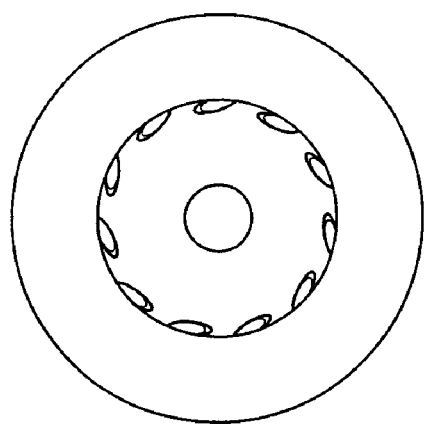

Inertia is the tendency of matter to remain at rest, if at rest, or, if moving, to keep moving in the same direction unless acted upon by some outside force. A motor and impeller suitable for use with the invention should be of sufficiently low inertia. In use for a CPAP device, the motor typically operates at several thousand revolutions per minute (RPM). If power is no longer supplied to a moving motor, the time it takes to slow down is a function of the inertia of the motor and impeller and the air flow rate through the impeller. A given motor, impeller and volute combination will develop lower pressure air at a lower rotational speed. In a preferred form of the invention the inertia is less than 13,000 to 14,000 g. mm$^2$, preferably less than 13,600 g. mm$^2$. One form of suitable volute housing is shown in FIGS. 6–8, and one form of suitable motor and impeller is shown in FIG. 9. A suitable material for constructing the impeller is a glass filled polycarbonate such as GE LEXAN 3412R. Such a volute and impeller are found in the S7™ ELITE by ResMed Limited.

Inertia, or moment of inertia, is the term given to rotational inertia, the rotational analog of mass for linear motion. Moment of inertia is defined with respect to a specific rotation axis, in our case, the axis of the spindle in the motor. The moment of inertia of a point mass with respect to this axis is defined as the product of the mass times the distance from the axis squared. The moment of inertia of any extended object is built up from that basic definition.

Inertia for a complex article may be calculated using a computer package such as SolidWorks. The package takes the rotor, spindle, impeller and anything else that rotates, breaks it all into millions of blocks of mass, and adds all the individual Inertias together (J. L. Meriam and L. G. Kraige, Engineering Mechanics—Dynamics, John Wiley & Sons, Inc., 1998, pages 665–682).

Alternatively, one may calculate the moment of inertia from first principles. The rotor may be broken into simple shapes such as discs, cylinders, spheres etc. For these shapes, the inertia values can be calculated analytically and then added together to get the total moment of inertia.

A CPAP device such as the S7 ELITE manufactured by ResMed Limited may be adapted to incorporate our invention. Generally, the controller of the CPAP apparatus according to an embodiment of our invention is programmed to deliver a CPAP pressure in the range of 4 to 25 cm H2O. In an automatically adjusting form of the apparatus, such as the AutoSet SPIRIT and as taught in the abovementioned U.S. Pat. No. 5,704,345, the CPAP apparatus is programmed to increase the CPAP pressure to overcome or prevent partial or complete obstructions of the airway as indicated by the presence of snoring, apneas or flow flattening.

The controller 14 is programmed to slightly reduce the pressure of air in the patient interface delivered to the patient during the exhalation portion of the respiratory cycle of the patient from the treatment pressure recommended by the patient's physician. The amount of the reduction is, in one form, determined by a setting accessible through the switches 26 on the CPAP apparatus. For example, the controller may be programmed to provide four different levels of pressure reduction during exhalation, each level leading to a reduction by an additional 1 cm H2O pressure (comfort mode). For example, when the CPAP pressure is set to deliver air at 15 cm H2O pressure to the patient interface during inhalation and the comfort mode is set to level 2, the pressure will be reduced to 13 cm H2O during exhalation.

In another form of our invention, the amounts of reduction are approximately 2.5, 3, and 3.5 cm H2O; in further forms of our invention, the amounts of reduction are approximately 1, 2 and 3.5 cm H2O, and 1, 2 and 3 cm H2O.

In one preferred form of our invention, the maximum amount of pressure reduction is fixed by the level setting, and during exhalation the pressure Will not drop lower than the predetermined amount. Preferably, the mask pressure will not drop lower than 4 cm H2O.

In one form of our invention, the pressure is reduced from the CPAP pressure by the amount set according to the level setting when a flow signal monitoring the respiratory flow is indicative of the beginning of the expiratory portion of the patient's respiratory cycle. The pressure remains at the lower level until an indication of the beginning of inspiration is detected, whereupon the pressure is returned to the CPAP pressure.

In another form of our invention, the pressure is reduced from the CPAP pressure by the amount set according to the level setting when a flow signal monitoring the respiratory flow is indicative of the beginning of the expiratory portion of the patient's respiratory cycle. The pressure remains at the lower level until either an indication of the beginning of inspiration is detected, or an apnea is detected, whereupon the pressure is returned to the CPAP pressure.

Upon detection of an apnea, the pressure may remain at the higher level during both inhalation and exhalation. In addition, upon the detection of cessation of the apnea (i.e., resumption of normal breathing) or expiration of a preset period of time, the reduction of pressure during exhalation mode may be resumed.

In accordance with a feature of our invention, the pressure reduction is effected by "freewheeling" the motor. That is, when exhalation is detected, energization of the motor windings is temporarily stopped, allowing the rotor to slow down eventually and resulting in a reduced pressure of air being delivered to the patient interface. This approach provides a gradual reduction in pressure that is particularly comfortable. Pressure in the patient interface is monitored and when the patient interface pressure drops to an acceptable level (as set by the "comfort" level), energization of the motor windings is resumed at a lower speed which is sufficient to maintain the patient interface pressure at a lower level. If a flow signal indicative of the beginning of inspiration is detected, the motor speed is increased so that it delivers the required CPAP pressure.

In general, the sequencing takes three steps:

(i) Upon detection of the transition from inhalation to exhalation, the motor is de-energized to allow it to freewheel.

(ii) When the pressure in the patient mask (or whatever interface is utilized) reaches a minimum pressure level during exhalation, the motor is re-energized and its speed is controlled so to maintain the pressure at a level suitable for exhalation.

(iii) Upon detection of the transition from exhalation to inhalation, the motor speed is increased to provide higher pressures in the patient mask suitable for inhalation.

Figure 2:
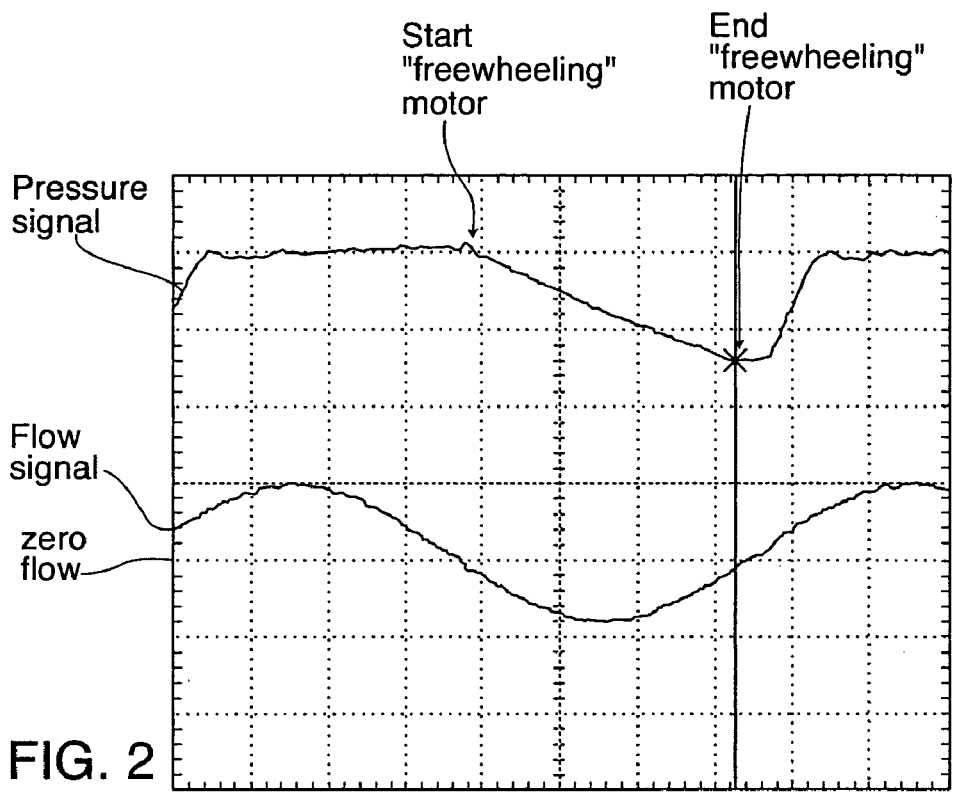
FIG. 2 shows the response of apparatus in accordance with an embodiment of the invention that uses freewheeling to slow the motor.

FIG. 2 is a screen from an oscilloscope showing two traces when apparatus in accordance with an embodiment of the invention is tested with a breathing machine delivering a sinusoidal breath with a tidal volume of 500 ml and 15 breaths per minute. The upper trace shows a pressure signal. The lower trace shows a flow signal. The flow signal is used to detect at least one transition. The transition of the flow signal from a positive value to a negative value (a zero crossing) can be used to define the onset of exhalation. The transition of the flow signal from a negative value to a positive value (a zero crossing) can be used to define the onset of inhalation. When the flow signal is smaller than a threshold value, a zero-crossing is taken to have occurred. The threshold has the effect of adjusting the phase delay between the pressure and flow curves. The larger the threshold, the more confidence there can be that a zero-crossing has been detected reliably. However, there is increased uncertainty in when the transition occurred, potentially leading to a phase delay and reduced synchronicity. Defining an inspiratory flow to be a positive value, the threshold for the transition from inhalation to exhalation is 0 to 5 l/min, preferably 1 l/min. The threshold for the transition from exhalation to inhalation is −4 to −1 l/min, preferably −1 l/min.

In another form of the invention, the threshold for the transition from inhalation to exhalation is in the range of −4 to −1 l/min, preferably, −1 l/min, and the threshold from exhalation to inhalation is in the range of 0 to 5 l/min, preferably 1 l/min. An advantage of this approach is that if there is a plateau region in the flow curve from exhalation to inhalation, as sometimes occurs, inhalation will not be triggered prematurely.

In a further form of the invention, flow is integrated to calculate a volume. Exhalation is taken to occur when the volume is negative, and inhalation is taken to occur when the volume is positive.

In general, in a device in accordance with the invention, specificity of the cycling/triggering threshold is favored over sensitivity.

The results of "freewheeling" indicate a long ramping down of approximately 3 to 4 cm H2O in approximately 1.7 seconds to the new set pressure during exhalation, and a fast rise time (approximately 350 to 800 ms) once inhalation begins. Rise time is a function of a number of factors including power supply and inertia. The long fall time is attributed to the inertia of the motor and no active breaking.

In other forms of our invention, pressure reduction is influenced by braking the motor during at least some of the time that it is freewheeling. Braking may be accomplished by shorting the windings. In one form of the invention, both pressure and flow are monitored by respective pressure and flow transducers. In other forms of the invention, pressure is estimated from the motor speed.

Figure 3:
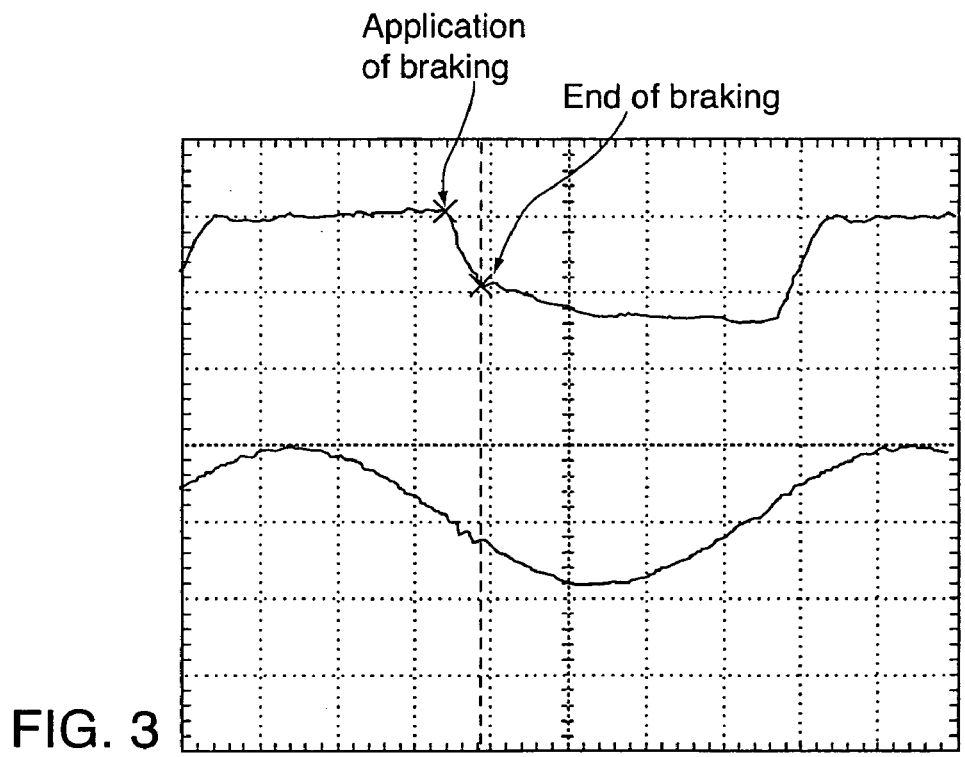
FIG. 3 shows the response of apparatus in accordance with an embodiment of the invention that uses a combination of braking and freewheeling.

FIG. 3 shows the same set of curves as FIG. 2. However, in FIG. 3, following the zero crossing from inhalation to exhalation, a brake is applied causing the pressure to fall approximately 2.7 cm H2O in 240 ms. The braking times used are a function of the error, that is, the difference between the measured pressure and the target pressure. The greater the error, the longer the duration of braking. As the error decreases, shorter braking is used. Thus the duration of the braking time is a function of the error. In FIG. 2, braking durations of 50 ms on/off, 30 ms on/off and 10 ms on/off were used. Hence the pressure reduction occurs as a result of a combination of freewheeling and braking of the motor.

In one form, the brake is applied and not released until the pressure on the transducer is the same as the new set pressure for the exhalation cycle. If the brake is on when inhalation begins (i.e., Respiratory Flow, $R_f > H_{TH}$), then the brake is released and the set pressure returned to the CPAP treatment pressure.

A state machine was used to apply the brake in on/off cycles with the period getting faster as the set pressure is reached.

The application of a switching brake can be further improved by taking into account braking over large and small pressure drops.

An algorithm for accomplishing the pressure reduction is as follows:

1) Detect zero crossing.
2) Set Target pressure=(Treatment pressure−Selected pressure reduction).
3) Calculate pressure error=Current pressure−Target pressure
4) While pressure error>=a threshold, brake the motor with a preferred duty cycle.

Figure 4:
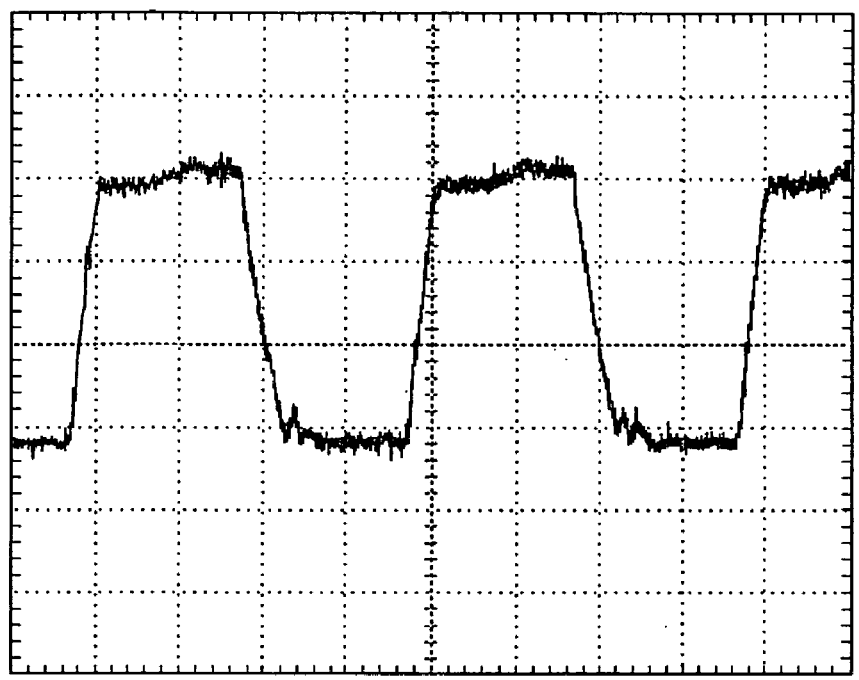
FIG. 4 shows the response of apparatus in accordance with an embodiment of the invention that uses braking with a 33% duty cycle.

In one form, dithered braking is used, that is, braking the motor in short bursts, for example a 25%–50%, preferably 33%, duty cycle (e.g., 10 ms brake on, 20 ms brake off). The size of the duty cycle required to achieve the required pressure reduction is a function of inertia. With a motor and impeller combination as described above, use of a shorter duty cycle—say 10%—is insufficient to slow the motor down to achieve the desired pressure reduction in the desired time. However, with the use of a lower inertia motor and impeller, it may be possible to achieve the desired pressure reduction with a 10% duty cycle. Furthermore, while with the preferred motor and impeller use of a duty cycle greater than about 50% can cause pressure spikes, when other motors and impellers are used it may be possible to use a duty cycle greater than 50%. FIG. 4 shows the response of apparatus when the braking has a 33% duty cycle.

The size of the threshold is dependent on the duty cycle used to brake the motor. With a 33% duty cycle, the threshold is set to 0.5–0.9 cm H2O, preferably 0.5 cm H2O. With 25% duty cycle, a threshold in the range of 0.2–0.7 cm H2O would be used and with 50% duty cycle a threshold in the range of 0.8–1.4 cm H2O would be used.

Since acceleration of the motor from a lower speed to a speed sufficient to provide the therapeutic pressure takes a finite time, the increase in pressure from the lower "comfort" pressure to the treatment pressure also requires a finite time. The time delay could lead to a reduced synchrony between patient and blower. In this form of the invention, instead of waiting until the onset of inhalation is detected (for example, by the flow signal changing from a negative to a positive signal), an attempt is made to predict when inhalation will occur and to coordinate the increase in pressure to maintain synchrony.

Figure 5:
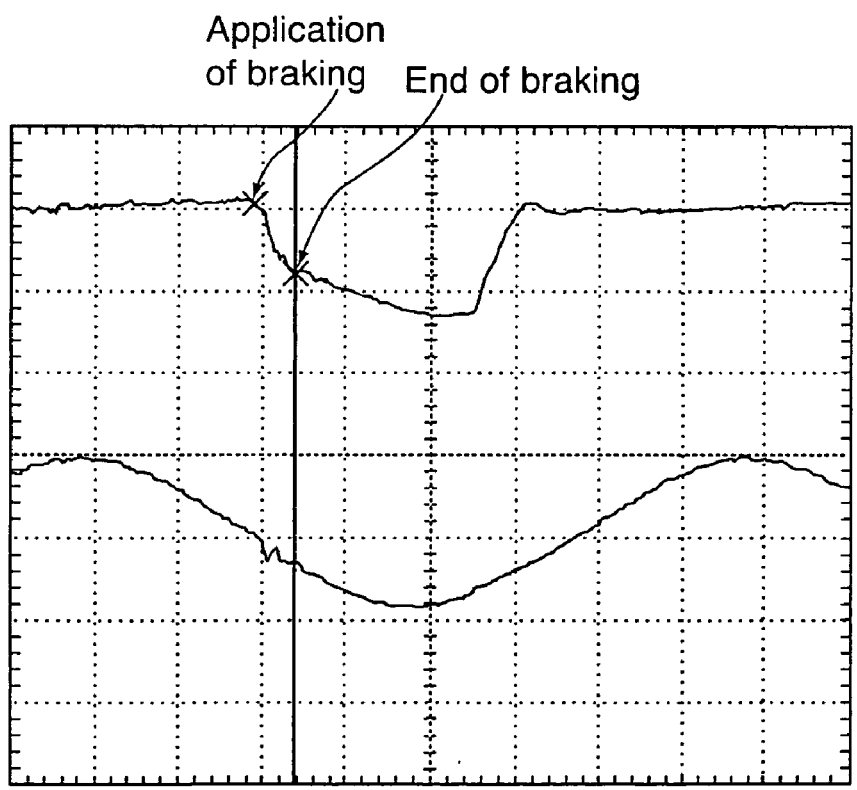
FIG. 5 shows the response of apparatus in accordance with an embodiment of the invention that uses negative peak detection to determine when to increase the pressure.
Figure 6C:
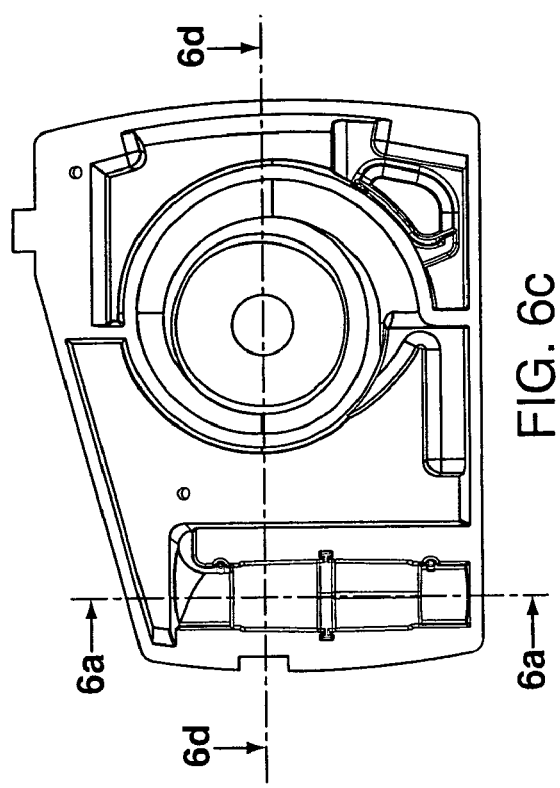
FIGS. 6a–d show various views of a lower volute suitable for use with an apparatus in accordance with an embodiment of the invention.
Figure 6D:
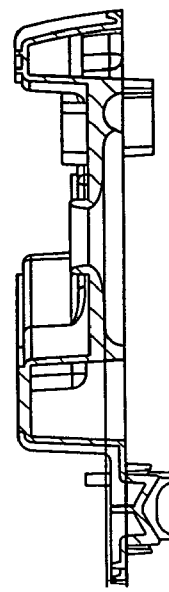
Figure 6A:
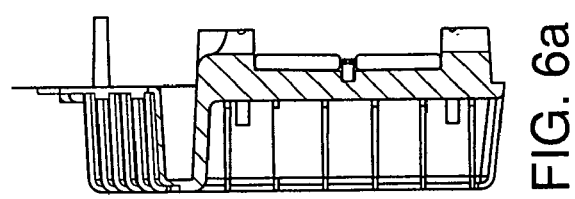
Figure 6B:
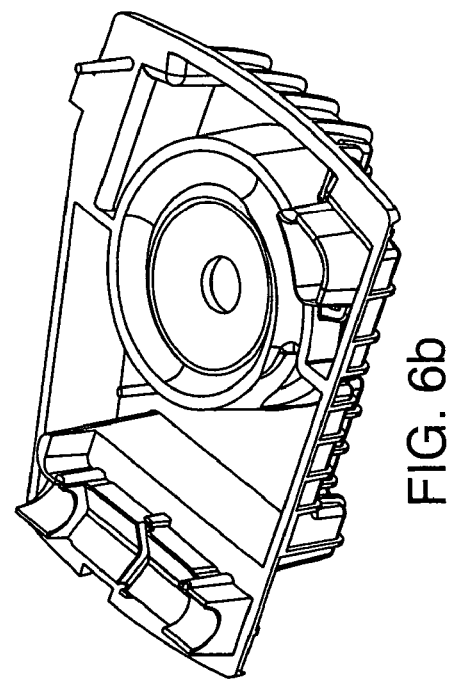
Figure 7D:
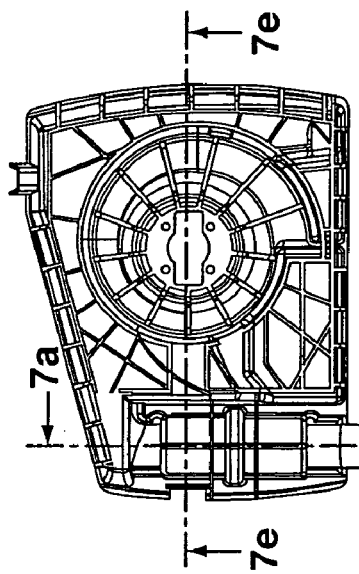
FIGS. 7a–f show various views of an upper volute suitable for use with an apparatus in accordance with an embodiment of the invention.
Figure 7E:
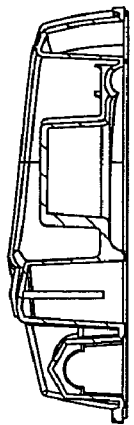
Figure 7F:
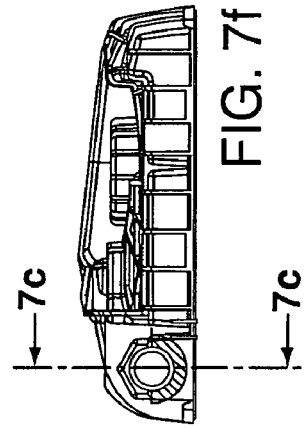
Figure 7C:
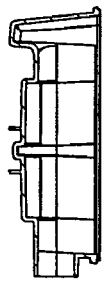
Figure 7A:
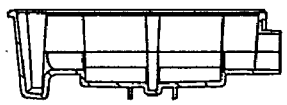
Figure 7B:
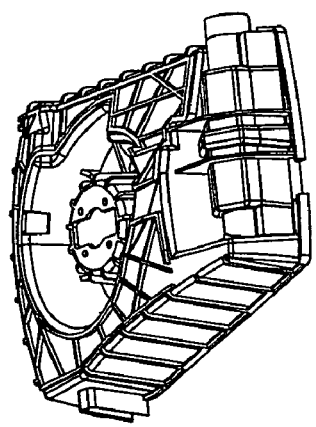

In one form of our invention, a negative peak detector is used to allow the pressure to start to ramp up at the apex of the exhalation cycle to allow delivery of treatment pressure to be stable before the inhalation cycle begins, as shown in FIG. 5. This method uses the previously described low threshold, with the high threshold being replaced with a negative peak detector.

In another form of our invention, we use the following method to attempt to eliminate false negative peaks. A running average of flow is calculated from three points spaced 10 ms apart. An hysteresis threshold may be fitted to the moving average. This embodiment can be improved by modifying the thresholds in the peak detection algorithm or modifying the approach taken to find the negative peak (for example, filtering and calculating the differential). Negative peaks can also be detected using the techniques for detecting minima, such as those in "Minimization or Maximization of Functions" Chapter 10, Numerical Recipes, W. H. Press et al., 1986, Cambridge University Press, ISBN 0 521 30811 9.

Other techniques may be used to predict when inhalation will occur, to coordinate the increase in pressure and to maintain synchrony. For example, in another form of the invention, an average exhalation cycle duration, $t_d$, is calculated from consecutive zero-crossings of flow and the time necessary for an increase in pressure from the lower "comfort" pressure to the therapeutic pressure, $t_p$. Once exhalation is detected, a timer $t_e$ records the time since the start of exhalation. Acceleration of the motor from the lower speed to the higher speed is initiated when $t_e = t_d - t_p$.

Figure 10:
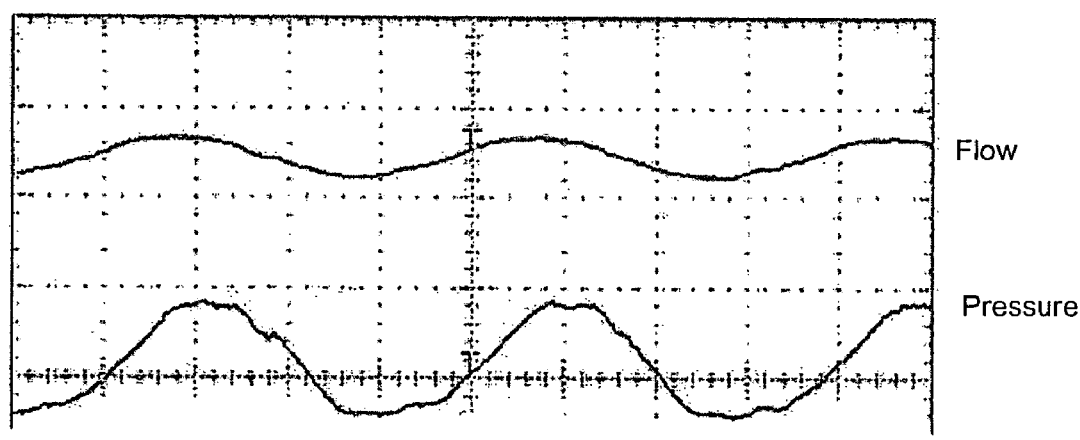
FIG. 10 shows the response of an apparatus in accordance with an embodiment of the invention with CPAP pressure set to 15 cm H$_2$O and a level of reduction of 3 cm H$_2$O, the upper curve showing flow, the lower curve showing pressure, and each horizontal grid corresponding to approximately 1 second.
Figure 11:
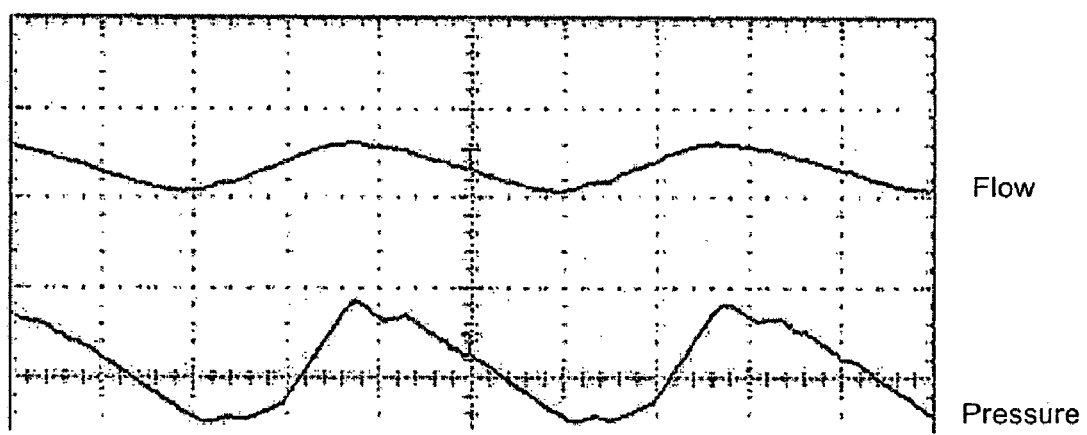
FIG. 11, with the same horizontal and vertical scales as FIG. 10, shows a view similar to that of FIG. 10, but with the CPAP pressure set to 10 cm H$_2$O.

The rate of pressure decrease during free-wheeling can depend upon the inhalation pressure immediately prior to the free-wheeling onset. For example from an inhalation pressure of 15 cmH2O, a 3 cm H2O drop in pressure may occur in approximately 1 second. See FIG. 10. In contrast from an inhalation pressure of 10 cm H2O a 3 cm H2O drop in pressure may occur in approximately 2 seconds. See FIG. 11. Thus in accordance with an embodiment of the invention there is provided a a means for achieving an adjustable rate of exhalation pressure relief.

An advantage of the present invention in which the pressure reduction that occurs is limited by an adjustable amount is that the limitation ensures adequate $CO_2$ washout and/or maintenance of an open airway. For example, in a CPAP system in which an exhalation pressure reduction is purely dependent on exhalation flow, the CPAP pressure during exhalation may drop below the pressure necessary to ensure adequate $CO_2$ washout, which is generally about 4 cm H2O. Accordingly, an improvement can be made to a device such as that in U.S. Pat. No. 5,535,738 or the Respironics Inc. BiPAP ventilator with C-Flex mode, wherein during an exhalation portion of the cycle, pressure is allowed to follow expiratory flow rate, but may only fall to a threshold. Thus, patient interface pressure never falls below the pressure adequate to insure sufficient $CO_2$ washout and/or to maintain an open upper airway.

The freewheeling technique of this invention has been described thus far as being applied during the administration of repetitive therapy cycles. However, there are at least two other uses of the technique. One is during the ramp phase feature available on many CPAP therapy machines, where the mask pressure builds up towards the treatment pressure during the ramp phase, as the patient tries to fall asleep. See U.S. Pat. Nos. 5,199,424, 5,522,382 and 6,705,351. For example, during the ramp phase, the inspiratory pressure may be constant during a cycle (while increasing from cycle to cycle), but the expiratory pressure may be increasing from cycle to cycle but also controlled by the motor or blower rotor freewheeling in accordance with the teachings of the present invention. It is also possible to disable the freewheeling technique at the end of the ramp phase, i.e., once the therapeutic pressure is reached. It may also be considered appropriate to taper the end of the freewheeling technique ramp phase so as to achieve a smooth transition to the therapeutic CPAP pressure level. This tapering would occur by gradually reducing the pressure differential between exhalation and inhalation over successive breaths. Preferably, this would occur during the last minute of the ramp phase and would equate to about 15 average breaths. This tapering is intended to reduce disturbance to and promote the comfort of the patient.

By disabling the freewheeling technique at the end of the ramp phase the patient is provided with maximum comfort while trying to fall asleep (i.e., during the ramp phase) without the freewheeling technique interfering with the clinically determined therapeutic pressure during sleep (i.e., during the therapeutic phase). Similarly, the freewheeling technique of the present invention can be used during the "settling time" phase of auto-titrating positive airway pressure (APAP) such as is available with a ResMed AutoSet® SPIRIT CPAP apparatus. During "settling-time" a constant but low mask pressure is provided so as to allow the patient to drift into sleep. At the end of the "settling time" the APAP provides the patient with variable therapeutic treatment pressure as determined appropriate by the treatment algorithm. By applying the freewheeling technique of the present invention only during "settling time," patient comfort may be enhanced during the transition to sleep while not compromising the actual therapy. Of course, if it is considered clinically undesirable for the patient interface pressure to go below the low pressure set for "settling time" phase, then it would be appropriate not to engage the freewheeling technique during that phase. Alternatively, the settling time phase pressure may be set at a level that would be sufficient for the freewheeling technique to be enabled but not drop the pressure during exhalation to a level that is lower than a predetermined clinically acceptable level. Disabling the freewheeling technique at the end of the ramp phase of CPAP or at the end of the "settling time" of APAP avoids the occurrence of freewheeling induced insufficient pressure support or insufficient $CO_2$ washout during the therapeutic phase.

Although the invention has been described with reference to particular embodiments, it is to be understood that these embodiments are merely illustrative of the application of the principles of the invention. Numerous modifications may be made therein and other arrangements may be devised without departing from the spirit and scope of the invention. For example, while in the illustrative embodiment, a flow signal is used to determine the transition between inhalation and exhalation, other signals, such as pressure, may be used. Combinations of signals, such as flow and effort, may also be used, and freewheeling may be used to control or reduce patient interface pressure swing.

We claim:

1. In a CPAP apparatus having an electric motor, an impeller rotated by the motor, a patient interface, an air delivery conduit for delivering air from the impeller to the patient interface, a mechanism for determining the pressure in the patient interface, and a control mechanism that causes air to be delivered at a desired pressure to the patient interface, and that detects transitions between inhalation and exhalation of a respiratory cycle of a patient; a method of controlling the motor operation during a sequence of respiratory cycles comprising the steps of:

(i) upon detection of the transition from inhalation to exhalation, de-energizing the motor to allow the motor to freewheel;

(ii) when the pressure in the patient interface reaches a minimum pressure level during exhalation, re-energizing the motor and controlling its speed so to maintain the pressure at a level suitable for exhalation; and (iii) upon detection of the transition from exhalation to inhalation, increasing the motor speed to provide higher pressures in the patient interface suitable for inhalation, wherein during a ramp phase the motor speed is controlled in step (iii) so as to increase the pressure over successive respiratory cycles and to provide a substantially constant pressure during any single respiratory cycle while increasing the substantially constant pressure over successive respiratory cycles.

* * * * *